United States Patent [19]

Pauley et al.

[11] Patent Number: 5,206,165

[45] Date of Patent: Apr. 27, 1993

[54] IMMORTAL HUMAN MAMMARY EPITHELIAL CELL SUBLINES

[75] Inventors: Robert J. Pauley, Farmington; Paine Terry J., Detroit; Herbert D. Soule, Dearborn, all of Mich.

[73] Assignee: Michigan Cancer Foundation, Detroit, Mich.

[21] Appl. No.: 727,518

[22] Filed: Jul. 9, 1991

[51] Int. Cl.$^5$ .......................... C12N 5/00; C12N 5/08
[52] U.S. Cl. ............................... 435/240.2; 435/240.1
[58] Field of Search ........................... 435/240.1, 240.2

[56] References Cited

U.S. PATENT DOCUMENTS 4,423,145  12/1983  Stampfer et al. ............... 435/240.23
4,808,532   2/1989  Stampfer .......................... 435/240.2
5,026,637   6/1991  Soule et al. ....................... 435/240.2

OTHER PUBLICATIONS

Bano et al, J. of Biological Chemistry, 265 (4), Feb. 5, 1990, pp. 1874–1880.

Trask et al, Proc. Natl. Acad. Sci USA, 87, pp. 2319–2323, Mar. 1990.

Zajchowski et al, Proc. Natl. Acad. Sci USA, 87, pp. 2314–2318, Mar. 1990.

Eldridge et al, Cancer Research, 49, pp. 4326–4331, Aug. 1, 1989.

*In Vitro*, vol. 20, No. 8, (Aug. 1984).

In Vitro Cellular and Development Biology, vol. 22, No. 1 (Jan. 1986).

Abstract 1780, Proc. AACR, vol. 29, 448 (Mar. 1988).

*Primary Examiner*—Douglas W. Robinson
*Assistant Examiner*—Susan M. Weber
*Attorney, Agent, or Firm*—Dykema Gossett

[57] ABSTRACT

Two immortalized human mammary epithelial cell sublines are provided. The sublines do not undergo terminal differentiation and senescence upon exposure to high calcium concentrations. The sublines exhibit positive reactivity with milk-fat globule membrane and cytokeratin anti-sera and are non-tumorigenic in athymic mice. The sublines are useful in evaluating the capacity of preselected agents to bring about a change in epithelial cell growth and in the production of proteins.

4 Claims, 1 Drawing Sheet

IMMORTAL HUMAN MAMMARY EPITHELIAL CELL SUBLINES

The discovery of the present invention was supported by NIH Grants CA22453 and RR05529 and an institutional grant from the Detroit United Way.

FIELD OF THE INVENTION

The present invention relates generally to human epithelial cells. More specifically, the present invention provides a new immortalized human mammary epithelial cell line and methods of using the novel cells in research and industry.

BACKGROUND OF THE INVENTION

The principle of limited cell division potential of somatic cells in vitro is well established. In a number of fields, researchers utilize somatic cell cultures derived from normal tissues in order to study the mechanisms underlying intercellular interaction and cellular response to various stimuli. These include such diverse pursuits as evaluating the carcinogenicity of selected agents, determining the activities of various hormones, monitoring the reactions of chemotherapeutic agents, and in general studying the metabolic characteristics of a given cell type. However, the phenomenon of limited cell division of normal cells complicates these efforts and often prevents long-term evaluation of cell sensitivity and induced expression.

More specifically, the study by oncologists of neoplastic transformation of epithelial cells has been severely limited by the relatively limited in vitro population longevity. This has led to the use of human fibroblast cultures which have greater in vitro longevity as the accepted model for transformation studies. However, it has been noted that the analogy drawn between these two distinct cell-types is tenuous at best and that the lack of a true long-term epithelial model has hindered cancer research. This is despite the fact that neoplasms of epithelial origin are the most prevalent type of cancer in humans.

In particular, it is known that conventional human mammary epithelial cells generally have at most a limited cell division potential (generally about 13 doublings). In "A Simplified Method For Passage and Long-Term Growth of Human Mammary Epithelial Cells," *In Vitro Cellular and Developmental Biology*, Vol. 22, No. 1, January, 1986, which is incorporated herein by reference, a method of culturing non-neoplastic human mammary epithelial cells which extends the population longevity of these cells beyond the previously reported limit of 13 doublings to more than 50 generations was reported. Longevity was achieved by reducing the Ca++ concentration of the media which in turn reduced an inhibition effect in which glucocorticoids induced terminal differentiation. A significant observation which was made in these studies was that conventional human mammary epithelial cells in culture media greater than 0.06 mM ionic calcium underwent terminal differentiation after only three or four passages from primary culture.

More recently, in U.S. Pat. No. 5,026,637, filed Feb. 28, 1989, an immortal human mammary epithelial cell line, which contained sublines designated MCF-10A and MCF-10F, was described. This earlier patent application, which is assigned to the same assignee as the present application, is hereby incorporated by reference. The cell sublines MCF-10A and MCF-10F demonstrated unlimited cell division potential and produced mammary epithelial cell proteins. These cell sublines were capable of subsisting in a high-calcium media without undergoing calcium-induced cellular senescence. Both earlier cell sublines MCF-10A and MCF-10F were non-tumorigenic in athymic mice and demonstrated a characteristic response to treatment with insulin, epidermal growth factor, and cortisol.

A new immortal human mammary epithelial cell line, described herein, has been developed. This cell line (designated MCF-12) was derived from reduction mammoplasty tissue from a nulliparous postmenopausal subject. Cell line MCF-12 became immortal after exposure to elevated temperatures. Cell line MCF-12 consists of two sublines, designated MCF-12A and MCF-12F.

It is desirable to provide several genetically different, non-neoplastic epithelial cell lines which could be cultured indefinitely to permit long-term evaluation of suspected reactive agents. It would also be desirable to provide such cell lines which produce a complement of proteins characteristic of normal human breast epithelial cells. It would be further desirable to provide a method by which epithelial cell sensitivity to suspected reactive agents and cellular expression thereby induced could be studied on a long-term basis. Different interactions of the reactive agents and cellular expression in the various cell lines and sublines may prove especially useful. The present invention satisfies these goals by providing a new non-neoplastic human mammary epithelial cell line for use in cell culture studies.

SUMMARY OF THE INVENTION

In accordance with the present invention there is provided in one aspect a cell line of immortal non-neoplastic human mammary cells, the cell line being designated MCF-12, which have unlimited cell division potential and which produce mammary epithelial cell proteins. Cell line MCF-12 consists of two sublines, designated as MCF-12A and MCF-12F. The novel cell sublines of the present invention are provided as biologically pure cultures and are capable of subsisting in a high-calcium media without undergoing calcium-induced cellular senescence. MCF-12A and MCF-12F are non-tumorigenic in athymic mice.

In still another aspect, the present invention provides a method for testing the long-term biological activity of a preselected agent on epithelial cell growth in vitro which comprises the steps of exposing a culture of immortalized human mammary epithelial cells, as provided by the present invention under the designations MCF-12A or MCF-12F, to a preselected agent and monitoring cellular sensitivity and/or induced altered cellular expression.

Hence, it is an object of the present invention to provide two immortal sublines of a non-neoplastic human mammary epithelial cell line to be used as models in epithelial cell studies. Combined with the sublines described in the previous patent application described above and Applicants' copending application U.S. Ser. No. 07/727,519, filed Jul, 9, 1991 entitled "Immortal Human Mammary Epithelial Cell Line" six different sublines of non-neoplastic human mammary epithelial cells are now available for such modeling. This copending application, which is assigned to the same assignee as the present invention and is hereby incorporated by reference, describes a new immortal epithelial cell line with two sublines, which are designated MCF-10-2A and MCF-10-2F.

It is a further object of the present invention to provide a method by which the activities of preselected agents on epithelial cells can be observed over extended periods.

These and other objects and advantages of the present invention will become apparent through the following description of the preferred embodiments of the invention and with reference to the drawings in which:

DESCRIPTION OF THE PREFERRED EMBODIMENTS

Figure 1:
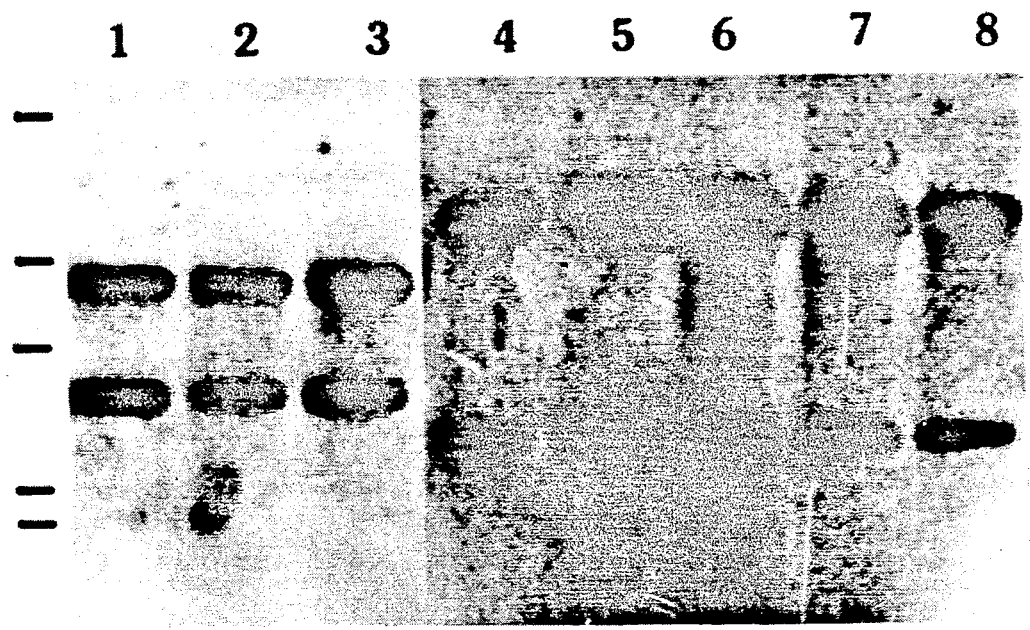
FIG. 1 is the DNA fingerprint of various immortal MCF-12A and MCF-12F cell cultures of this invention. Also included are the DNA fingerprints of precursor (mortal) cell cultures and the immortal MCF-10A and MCF-10F cultures as well as immortal MCF-10-2A and MCF-10-2F cell cultures for comparison purposes.

The present invention provides two sublines of a non-neoplastic immortal human breast epithelial cell line. This cell line, designated MCF-12, consists of two sublines designated as MCF-12A and MCF-12F. Cultures of MCF-12A and MCF-12F have been deposited on Jun. 20, 1991, with the American Type Culture Collection (ATCC) at 12301 Parkland Drive in Rockville, Md., 20852 under the Budapest Treaty on the International Recognition of the Deposit of Microorganisms for the Purposes of Patent Procedures. The following ATCC Registration Numbers have been assigned: for subline MCF-12A, Registration No. ATCC CRL 10782; and for subline MCF-12F, Registration No. ATCC CRL 10783.

The immortal cell line of the present invention comprises human mammary epithelial cell sublines that are characterized by unlimited (immortal) cell division potential. The novel cell sublines of the present invention are resistant to high-calcium induced senescence which is typical of most prior art human mammary epithelial cells. MCF-12A and MCF-12F express cytokeratins, milk-fat globule antigens (or polymorphic epithelial mucin) and other conventional mammary epithelial markers. These sublines are growth-responsive to insulin, epidermal growth factor, cholera enterotoxin and cortisol. The novel sublines of the present invention are non-tumorigenic in athymic mice. These sublines also demonstrate dome formation in confluent cultures characteristic of epithelial cells. The sublines MCF-12A and MCF-12F appear to be immortal with retention of many characteristics of normal human breast epithelium and its conventional phenotypes.

MCF-12A and MCF-12F were likely produced by in vitro treatment of human mammary epithelial cells at elevated temperatures. In order to more fully understand the Applicants' novel cell lines, the protocols utilized in discovery of the present invention will now be fully explained for the MCF-12 cell line.

Except as noted below, the procedures used were essentially the same as used in preparing MCF-10A and MCF-10F sublines as described in U.S. Pat. No. 5,026,637. This immortal cell line (MCF-12) was derived from reduction mammoplasty tissue of a 63 year old, nulliparous postmenopausal woman. The non-malignant tissue exhibited fibrocystic disease and intraductal hyperplasia. The samples were observed for the presence of normally dense stroma and parenchyma, and then minced to fragments using a scalpel. These fragments were then further divided into cells and cell aggregates or organoids by treatment with collagenase and hyaluronidase using the procedures set forth in "Growth of Normal Human Mammary Cells In Culture," In Vitro, 615:415–425 (1980), which is incorporated herein by reference. Ten micrograms/ml insulin and 1.4 mM cortisol were included, with 10% serum in the digestion mixtures as detailed in "Renewal Inhibition of Human Mammary Cell Growth in Vitro: Cortisol and the Recruitment Cells to Terminal Differentiation," J. Cell Physiol., 116:385–396 (1983), which is incorporated herein by reference.

The resultant disassociated epithelium was then plated in primary culture as fully described in the immediately foregoing reference. Cell number of this diploid mortal culture was estimated from packed cell volumes. Primary cultures and succeeding cultures were generally cultured in 75 sq. cm (T-75) flasks. Mortal cells were subcultivated by passing free-floating cells. Cell viability was determined by the trypan blue exclusion test using a hemocytometer. Cell number and viability of the seed flasks were determined by performing a cell count when the nutrients were replenished. The number of doublings that occurred during the extended time periods in culture was calculated by determining total cell number released from a constant cell number that remained attached in confluent cultures.

During these experiments, Applicants were able to significantly extend the population longevity of epithelial cells without the continuous use of high calcium concentrations or enzymatic transfers as is more fully disclosed in "A Simplified Method For Passage and Long-Term Growth of Human Mammary Epithelial Cells," In Vitro, Vol. 22, No. 1 (January 1986). The sublines of this invention were derived from the diploid mortal culture which was cultured in a low calcium medium ($<0.06$ mM $Ca^{++}$) containing 5% chexlexed (divalent ion-free) equine serum.

After 1717 days in vitro the entire culture, consisting of passages 1 through 15, was accidentally exposed to 45° C. for as long as 72 hours. (The temperature before and after this event was maintained at 37° C.) Over 95 percent of the cells in each T-75 flask were killed by the 8° C. temperature increase. Only cells in passages 5 and 6 survived this crises event. Twenty two days after this exposure, the surviving culture produced free-floating cells capable of reattaching in new flasks. This culture ceased to undergo calcium induced senescense and has been designated as the MCF-12 cell line. Two sublines, MCF-12F and MCF-12A, were established at 1746 and 1773 days, respectively, in vitro. Subline MCF-12F was maintained in a low calcium, serum-containing medium. Subline MCF-12A was created by plating the cells in medium with conventional $Ca^{++}$ levels (1.05 mM) and 5% equine serum, then transferring serially with 0.05% trypsin-0.025% versene. As of Jun. 1, 1991, the MCF-12 cell line has been maintained for 312 days. The number of doublings that occurred was calculated by counting cells plated (F subline) or attached at day one (A subline) and cell number at transfer.

The culture media employed in these above-described studies will now be generally described. A 1:1 ratio of Dulbecco and Ham's F12 nutrients in admixture was utilized as the medium and was prepared de novo from the constituent compounds, using vitamins and amino acids obtained from Sigma Chemical Company. A basal salt solution was prepared without $CaCl_2$. Nutrients and salts were adjusted to a pH of 7.2 using HCl and NaOH and sterilized by filtration with 0.22 micrometer filters. Sterile $CaCl_2$ was added from 500 mM or 28.5 mM stock solutions to obtain 1.05 or 0.04 mM $Ca^{++}$, respectively. Divalent cations were removed from the serum using Chelex 100 (sodium form) obtained from Bio-Rad Laboratories pursuant to the method set forth in "Improved Methods for Reducing Calcium and Magnesium Concentration in Tissue Culture Medium: Application to Studies of Lymphoblast Proliferation In Vitro," In Vitro, 11:354-360 (1975), which is incorporated herein by reference. The serum was sterilized by filtration with a 0.45 micrometer filter and maintained at $-20°$ C. until use. Penicillin (100 U/ml), streptomycin (100 micrograms/ml), amphotericin B (0.25 micrograms/ml), cholera enterotoxin (100 ng/ml), and epidermal growth factor (20 ng/ml) were used to supplement the media, as was 5% horse serum. Insulin (10 micrograms/ml) and cortisol ($1.4 \times 10^{-6}$M) were also routinely included in the media. Powdered calcium-free media (Gibco, formula no. 90-5212 EG) can be employed instead of the individual ingredients of Dulbecco and Hamm's F-12 media.

As used herein, the term "immortal" or "immortalized" shall mean that, based upon current observations, these cells, under the culture conditions described herein, have shown no tendency to undergo terminal differentiation or cell senescence, but rather retain the capacity to divide indefinitely. By "non-neoplastic," it is meant that the novel cell lines of the present invention demonstrate no indicia characteristic of neoplastic cells other than immortality and are non-tumorigenic when injected in athymic mice.

The preferred culture medium for MCF-12F is a medium consisting of 95% Dulbecco and Ham's F-12 (1:1 ratio) nutrients and 5% equine serum with added epidermal growth factor (20 ng/ml), bovine insulin (10 mg/ml), cholera enterotoxin (100 ng/ml) and cortisol (1.4 mM), penicillin (100 units/ml), streptomycin (100 mg/ml), and amphotericin B (0.25 mg/ml) where the divalent ions were removed from equine serum with Chelex 100, the Dulbecco and Ham's F-12 nutrients were prepared without $CaCl_2$, and $Ca^{++}$ was added to obtain a 0.04 mM concentration. The preferred culture medium for MCF-12A was prepared in the same manner as the preferred MCF-12F medium except that the divalent ions were not removed from the equine serum and the $Ca^{++}$ was increased to a 1.05 mM concentration. MCF-12A is preferably grown as monolayers, transferred 1:25 weekly. MCF-12F is preferably grown as monolayers which yield free-floating cells and transferred 1:4 weekly with free-floating cells.

The protocol used to prepare the media used in the initial cultures of the tissue sample which gave rise to the MCF-12 cell line is described in detail in U.S. Pat. No. 5,026,637 and, therefore, need not be repeated here. The medium used in the initial culture of cell line MCF-12 was the same as for MCF-10-2 (described in Applicants' copending application) except that the MCF-12 medium was low $Ca^{++}$ (ca. 0.04 mM) with 5% chelexed (divalent ion-free) equine serum.

As stated, MCF-12A and MCF-12F are substantially normal, but immortalized, human mammary epithelial cell lines as determined by the following criteria: non-tumorigenicity in nude mice; presence of milk-fat globule membrane antigens; positive reactivity with cytokeratin antiserum; three-dimensional growth in collagen; growth control by hormones and growth factors; and dome formation in confluent cultures (1.05 mM $Ca^{++}$).

DNA fingerprinting of the cell lines of the present invention demonstrate that the MCF-12 cell line is a distinct continuous human cell line that was not contaminated with human breast tumor cell lines maintained in Applicants' laboratory, including the MCF-10 cell line described in U.S. Pat. No. 5,026,637 and the MCF-10-2 cell line described in Applicants' copending application. The DNA fingerprints of cell lines MCF-10, MCF-10-2, and MCF-12 are shown in FIG. 1. (Cell lines MCF-10 and MCF-10-2 are shown for comparison purposes.) The cell line DNA's were analyzed for the highly polymorphic human MUC1 locus which has a frequency of heterozygosity in HinfI digests of approximately 0.80 in the 156 chromosomes examined. HinfI digest of 2 mg of DNA were size fractionated, hybridized with the pmuc10 probe, and autoradiographed. The migration of lambda-HindIII size standards from 9.6 to 2.0 kb is indicated on the left-hand side of FIG. 1. The lanes and cell line DNA (with days of in vitro cultivation specified in parenthesis) in FIG. 1 are as follows: lane 1—MCF-12M (39 days); lane 2—MCF-12A (1893 days); lane 3—MCF-12F (1908 days); lane 4—MCF-10M (395 days); lane 5—MCF-10A (1702 days); lane 6—MCF-10F (1852 days); lane 7—MCF-10-2A (854 days); and lane 8—MCF-10-2F (852 days). Mortal cell line MCF-12M is the precursor of immortal cell sublines MCF-12A and MCF-12F of the present invention. Mortal cell line MCF-10M is the precursor of immortal cell sublines MCF-10A and MCF-10F, which are described in more detail in U.S. Pat. No. 5,026,637, and sublines MCF-10-2A and MCF-10-2F, which are described in more detail in Applicants' copending application. From this data it is concluded that the MCF-10, MCF-10-2, and MCF-12 cell lines are human, continuous breast cell lines; that MCF-10 and MCF-10-2 cell lines are of the same lineage; and that the MCF-12 cell line is of different lineage from the MCF-10 and MCF-10-2 cell lines.

Samples of MCF-12A cells injected into nude mice (5 week old athymic specimens) did not result in the formation of progressively growing tumors. Innoculum (ca. $10-15 \times 10^6$ cells) initially formed a mass (the largest averaging about 4.8 to 5.5 mm one week after injection) which gradually decreased in size until, by the fifth week, no mass was palpable or visible. The initial mass contained cells which organized as duct-like structures and had non-malignant cytologic features. Based on these observations, the MCF-12 immortal cell line does not appear to be tumorigenic.

Figure 2:
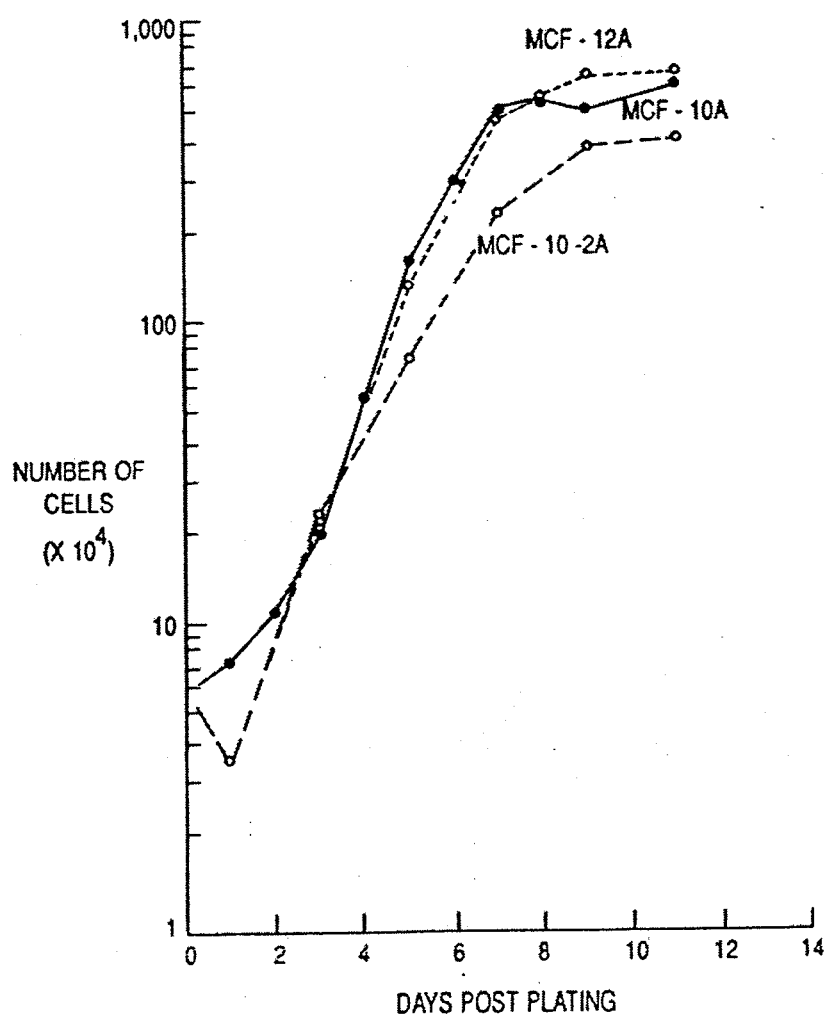
FIG. 2 shows the growth curves of immortal MCF-12A cell culture of the present invention. The growth curves of immortal MCF-10A cell culture and immortal MCF-10-2A cell culture are shown for comparison purposes.

Growth curves for the immortal cell lines MCF-10A (solid line), MCF-10-2A (dashed line), and MCF-12A (dotted line) are shown in FIG. 2. (Growth curves for MCF-10A and MCF-10-2A are included for comparison purposes.) In this Figure, the number of cells on a logarithmic scale is plotted against time in days. For MCF-10A, MCF-10-2A, and MCF-12A, the days in vitro at the initiation of the growth curves were 2172, 896, and 1906 days, respectively; and the passage numbers were 166, 77, and 32, respectively. Cells were plated at $6 \times 10^4$ cells per $T_{25}$ flask. The medium was changed on days 1, 3, 5, 7, and 9. Cell counts were determined with a hemocytometer following cell removal with trypsin-EDTA. Each measured point is the mean of three determinations; the standard deviation was less than 7 percent.

Based on the growth curves of FIG. 2, doubling times and saturation densities were determined for the three immortal cell lines. Doubling times were 19.0, 19.9, and 21.4 hours with total number of doublings at day 11 of 7.2, 6.2, and 6.7 for MCF-12A, MCF-10A, and MCF-10-2A, respectively. Thus, although MCF-12A has been immortalized for the shortest period, it shows the greatest growth potential. The saturation densities of MCF-12A and MCF-10A were essentially the same (ca. $2.6 \times 10^4$ cells/cm$^2$) and about 1.5 times greater than that of MCF-10-2A.

Two morphological cell types are apparent in the monolayers of breast cultures grown in normal calcium level (ca. 1.05 mM) medium: (1) large cells which have abundant cytoplasm, are irregular in shape, often vacuolated, and appear to be differentiating and senescing; and (2) small cells which are more uniform in shape, non-vacuolated, and form colonies. MCF-10-2A, which has been in vitro the shortest time and which was immortalized at a relatively early time, shows a mixed population of large and small cells. MCF-10A and MCF-12F show a more uniform small cell morphology. This may suggest that the process of immortalization either occurred in, or involved, the selection for the small cell phenotype. Domes are observed in MCF-10A and MCF-12A in areas of localized monolayers in preconfluent cultures (day 6). Domes are observed infrequently in MCF-10-2A and only in post confluent monolayers.

The MCF-12 cell line of the present invention was cytogenetically characterized using standard procedures. A culture of MCF-12A was harvested 51 days after the subline was established. Analysis showed that the chromosomes number ranged from 65-71 and all cells displayed consistent numerical and structural aberrations. They included two copies of a marker chromosome which resulted from unbalanced translocation between 1p and 2q. Four copies of #7, #8, #9, and #13 and two copies of #10, #11, #12, and #18 were uniformly seen. The cytogenetic characterization of MCF-12A is summarized in Table 1 which follows:

TABLE 1

| Chromosomes | MCF-12A |
|---|---|
| Number | 65-71 |
| X | 3 |
| 1 | 2 |
| 7 | 4 |
| 8 | 4 |
| 9 | 4 |
| 10 | 2 |
| 11 | 2 |
| 12 | 2 |
| 13 | 4 |
| 18 | 2 |
| 20 | 3 |
| 22 | 3 |
| Double minutes | 0 |
| Markers | two + der(1)t(1;10)(q11;p11) 2q+ |

The expression of various cytokeratins by the immortal cell line MCF-12 of the present invention, the immortal cell lines of U.S. Pat. No. 5,026,637, and the immortal cell line MCF-10-2 of Applicants' copending application were examined using the 2D gel western blot technique. Blots were prepared from each cell culture and reacted with anti-cytokeratin antibodies AE1 and AE3 which recognize all acidic and most basic cytokeratins, respectively, and with CK5 and K19.1 which are specific for cytokeratins 18 and 19, respectively. The three immortal cell lines showed similar luminal profile (cytokeratins 7, 8, 18, and 19) except for the variable expression of cytokeratin 19 which was lost in the MCF-10 and MCF-12 cell lines but retained in the MCF-10-2 cell line.

Immunoperoxidase staining with a monospecific antibody directed against cytokeratin 19 (antibody K19.1) was performed to determine if expression of this antigen could be correlated to the large or small cell type. The staining results are presented in the following Table 2.

TABLE 2

| Cell Culture | Days in vitro | Cytokeratin 19 Expression | |
|---|---|---|---|
| | | Large Cells | Small Cells |
| MCF-10M[661] | N.D. | | |
| MCF-10A | 1708 | − | −* |
| | 1933 | − | −* |
| MCF-10F | 843 | + | ± |
| | 2066 | − | −* |
| MCF-10M[341] | 440 | ++ | ++ |
| MCF-10-2A | 633 | ++ | + |
| | 911 | ++ | + |
| MCF-10-2F | 633 | ++ | ++ |
| | 911 | ++ | ++ |
| MCF-12M | 1493 | ++ | ++ |
| | 1663 | + | ± |
| MCF-12A | 1952 | − | −* |
| MCF-12F | 1952 | − | −* |

N.D., no data; cells were not available for assay due to low proliferation of MCF-10M[661] in low calcium, serum-free medium.
*Predominant cell type.
++ Heterogeneous staining, greater than 50% of the cells stained.
+ Heterogeneous staining, less than 50% of the cells stained.
± Staining in very few cells (<1%).
− No staining.

In addition to the novel cell lines of the present invention, the present invention provides a method for testing the effect of long-term exposure of epithelial cells in culture to a preselected agent. Accordingly, a culture of MCF-12A or MCF-12F would be exposed to a preselected agent, such as a suspected carcinogen. The cells would then be observed over an extended period of time to determine the effects, if any, of the exposure. In this manner, long-term studies of epithelial cells can be performed which were not previously possible.

In addition, the present invention could provide a method for producing proteins from human mammary epithelial cells which comprises the steps of culturing MCF-12A or MCF-12F and collecting proteins produced by the cells. The separation and isolation of proteins from somatic cells is well known in the art and suitable methods will be apparent.

The present invention has been described in connection with specific embodiments thereof; however, as will be appreciated by those skilled in the art, many modifications may be made to the invention without departing from the spirit and scope of the claims herein.

What is claimed is:

1. A biologically pure culture of an immortal human mammary epithelial cell subline designated Registration No. ATCC CRL 10782.

2. A biologically pure culture of an immortal human mammary epithelial cell subline designated Registration No. ATCC CRL 10783.

3. A cell culture containing cells from a biologically pure culture of an immortal human mammary epithelial cell subline designated Registration No. ATCC CRL 10782.

4. A cell culture containing cells from a biologically pure culture of an immortal human mammary epithelial cell subline designated Registration No. ATCC CRL 10783.

* * * * *

UNITED STATES PATENT AND TRADEMARK OFFICE
CERTIFICATE OF CORRECTION

PATENT NO. : 5,206,165

DATED : April 27, 1993

INVENTOR(S) : Pauley et al

It is certified that error appears in the above-identified patent and that said Letters Patent is hereby corrected as shown below:

On the title page, item [75], replace "Paine Terry J.", with -- Terry J. Paine --.

Column 4, line 17, replace "116:385-396", with -- 16:385-396 --.

Signed and Sealed this

Fifteenth Day of February, 1994

Attest:

BRUCE LEHMAN

*Attesting Officer*  *Commissioner of Patents and Trademarks*